US010716877B2

(12) United States Patent
Amiralian et al.

(10) Patent No.: US 10,716,877 B2
(45) Date of Patent: Jul. 21, 2020

(54) NANOCOMPOSITE ELASTOMERS

(71) Applicant: THE UNIVERSITY OF QUEENSLAND, St. Lucia, Queensland (AU)

(72) Inventors: Nasim Amiralian, Brisbane (AU); Darren James Martin, Brisbane (AU)

(73) Assignee: The University of Queensland, St Lucia, Queensland (AU)

( * ) Notice: Subject to any disclaimer, the term of this patent is extended or adjusted under 35 U.S.C. 154(b) by 93 days.

(21) Appl. No.: 15/533,622

(22) PCT Filed: Dec. 7, 2015

(86) PCT No.: PCT/AU2015/050773
§ 371 (c)(1),
(2) Date: Jun. 6, 2017

(87) PCT Pub. No.: WO2016/090425
PCT Pub. Date: Jun. 16, 2016

(65) Prior Publication Data
US 2017/0333602 A1    Nov. 23, 2017

(30) Foreign Application Priority Data

Dec. 8, 2014    (AU) ................................ 2014904956

(51) Int. Cl.
*A61L 31/04*      (2006.01)
*A61F 6/04*       (2006.01)
*C08L 5/14*       (2006.01)
*C09J 101/02*     (2006.01)
*C08G 18/40*      (2006.01)
*C09J 105/14*     (2006.01)
*C08L 1/02*       (2006.01)
*C08G 18/76*      (2006.01)
*C08G 18/64*      (2006.01)
*C08G 18/32*      (2006.01)
*C08L 75/04*      (2006.01)
*C08G 18/48*      (2006.01)
*C09J 175/04*     (2006.01)
*A61B 42/10*      (2016.01)
*A61M 25/10*      (2013.01)
*B29C 41/14*      (2006.01)
*C08K 7/02*       (2006.01)
(Continued)

(52) U.S. Cl.
CPC ............ *A61L 31/041* (2013.01); *A61B 42/10* (2016.02); *A61F 6/04* (2013.01); *A61M 25/1029* (2013.01); *B29C 41/14* (2013.01); *C08G 18/3206* (2013.01); *C08G 18/4081* (2013.01); *C08G 18/4854* (2013.01); *C08G 18/6484* (2013.01); *C08G 18/7671* (2013.01); *C08K 7/02* (2013.01); *C08L 1/02* (2013.01); *C08L 5/14* (2013.01); *C08L 75/04* (2013.01);

*C08L 75/08* (2013.01); *C09J 101/02* (2013.01); *C09J 105/14* (2013.01); *C09J 175/04* (2013.01); *A61M 2025/1031* (2013.01); *B29K 2075/00* (2013.01); *B29K 2105/124* (2013.01); *B29K 2201/00* (2013.01); *B29L 2031/7538* (2013.01); *B82Y 30/00* (2013.01); *C08K 2201/011* (2013.01); *C08L 2203/02* (2013.01)

(58) Field of Classification Search
CPC ... A61L 31/041; C08K 7/02; C08K 2201/011; A61B 42/10; A61F 6/04; B29C 41/14; B29K 2075/00; B29K 2105/124; B29K 2201/00; B29L 2031/7538; B82Y 30/00; C08G 18/3206; C08G 18/4081; C08G 18/4854; C08G 18/6484; C08G 18/7671; C08L 1/02; C08L 5/14; C08L 75/04; C08L 75/08; C08L 2203/02; C09J 101/02; C09J 105/14; C09J 175/04
See application file for complete search history.

(56) References Cited

U.S. PATENT DOCUMENTS

2010/0229873 A1*  9/2010  Hill ........................... A61F 6/04
                                                              128/844
2015/0111998 A1*  4/2015  Kawamoto ............... B29B 7/56
                                                              524/37

FOREIGN PATENT DOCUMENTS

WO    WO-2014200428 A1 *  12/2014  ......... H01L 29/0673

OTHER PUBLICATIONS

Visakh, P.M., Thomas, S., Oksman, K., Mathew, A.P., "Effect of Cellulose Nanofibers Isolated From Bamboo Pulp Residue on Vulcanized Natural Rubber", BioResources, 2012, 7(2), 2156-2168 (Year: 2012).*

(Continued)

*Primary Examiner* — James C Goloboy
(74) *Attorney, Agent, or Firm* — Nixon & Vanderhye P.C.

(57) ABSTRACT

A composite material comprising an elastomer and nanocellulose. The nanocellulose may comprise a nanocellulose material derived from plants having C4 leaf anatomy, or a nanocellulose material derived from a plant material having a lesser amount of lignin than hemicellulose, or a nanocellulose having a hemicellulose content of from 25% to 55% by weight of the nanocellulose material, or a nanocellulose comprising nanofibrils having a diameter of up to 5 nm, or a nanocellulose comprising nanocellulose material of plant origin comprising nanocellulose particles or fibres having an aspect ratio of at least 250, or the composite material having a stiffness of not greater than 2.5 times the stiffness of the elastomer without the nanocellulose material being present, or the nanocellulose particles or fibres being derived from a plant material having a hemicellulose content of 30% or higher (w/w). The nanocellulose may be derived from arid *Spinifex*.

29 Claims, 2 Drawing Sheets

(51) Int. Cl.
*C08L 75/08* (2006.01)
*B82Y 30/00* (2011.01)
*B29K 75/00* (2006.01)
*B29K 105/12* (2006.01)
*B29K 201/00* (2006.01)
*B29L 31/00* (2006.01)

(56) References Cited

OTHER PUBLICATIONS

Faruk, O., Bledzki, A.K., Fink, H.-P., Sain, M., "Biocomposites reinforced with natural fibers: 2000-2010", Progress in Polymer Science, 2012, 1552-1596 (Year: 2012).*

* cited by examiner

NANOCOMPOSITE ELASTOMERS

This application is the U.S. national phase of International Application No. PCT/AU2015/050773 filed Dec. 7, 2015 which designated the U.S. and claims priority to AU Patent Application No. 2014904956 filed Dec. 8, 2014, the entire contents of each of which are hereby incorporated by reference.

TECHNICAL FIELD

The present invention relates to nanocomposite elastomers. In particular, the present invention relates to nanocomposite elastomers that include nanocellulose fibres. The present invention also relates to articles manufactured from nanocomposite elastomers.

BACKGROUND ART

Elastomers, also known as rubber materials, have found application in a diverse range of areas including tyres, shoe soles, condoms, surgical and examination gloves, catheter balloons, mining equipment and shock adsorption for bridges just to name a few. In the majority of cases, successful adoption of elastomers in these and other applications has required some modification of the base elastomer to improve their mechanical properties, including the use of particulate or fibrous materials introduced into the elastomer matrix to act as reinforcing agents. Silica in particulate form is in widespread use to reinforce elastomers, typically providing increased strength, stiffness and toughness to a base elastomer. Newer materials being investigated as reinforcing agents for elastomers include carbon nanotubes, graphene and nanoclay particles.

In the last few decades, the use of natural fibres to reinforce polymer composites has been increasing because of their sustainability, renewability, biodegradability, low thermal expansion, manufacturer-friendly attributes such as low density and abrasiveness, excellent mechanical properties such as very high specific stiffness and strength and consumer-friendly attributes such as lower price and higher performance. A typical natural fibre consists of several or more nanocrystalline elementary fibrils formed by cellulose chains (homopolymers of glucose), concreted by/in a matrix containing lignin, hemicellulose and other components. The nanofibrils consist of monocrystalline cellulose domains linked by amorphous domains. Amorphous regions act as structural defects and can be removed under acid hydrolysis, leaving cellulose rod-like nanocrystals, which are also called whiskers, and have a morphology and crystallinity similar to the original cellulose fibres. Depending on the source of cellulose, the cellulose content varies from 35 to 100%. These fibers exhibit extraordinarily higher mechanical properties (stiffness/strength) at nanoscale phases than at the microscale or in their natural state. In recent years, these nanocrystalline cellulose fibres have been explored as biologically renewable nanomaterials that can be applied in several engineering applications.

While numerous methods have been explored for the production of microfibrillated cellulose (MFC), which by definition (Reference: Robert J. Moon, Ashlie Martini, John Nairn, John Simonsen and Jeff Youngblood, 'Cellulose nanomaterials review: structure, properties and nanocomposites' Chem. Soc. Rev., 2011, 40, 3941-3994), consists of cellulose fibres with diameters in the range of 20-100 nm and a length range of between 0.5 and tens of μm, the production of nanofibrillated cellulose (NFC; also known as cellulose nanofibres CNFs)), and cellulose nanocrystals (CNCs), is more challenging due to the requirement to separate or deconstruct the cellulose fibres to a much greater degree. Attempts to date to produce these two types of nanocellulose (CNCs and NFCs), have focussed on the use of chemical, physical, mechanical and enzymatic pretreatments alone or in combinations thereof. For NFC, the prior art refers to a fibre diameter in the range of 3-20 nm and a length in the range between 0.5 and 2 μm. For CNC, the prior art refers to fibre diameters in the range of 3-20 nm and length up to 500 nm (except the special example of tunicate CNCs or t-CNCs, which have a higher aspect ratio).

Although both CNCs and NFCs are nanocellulose materials, they exhibit different morphologies. CNCs are typically highly crystalline rod shaped particles with typical dimensions ranging from 5 to 20 nm in diameter and from 100 to 500 nm in length. On the other hand, NFCs have a diameter typically in the range of 5 to 20 nm and lengths within the micron scale. NFCs might be considered to be bundles of elementary cellulose fibrils (also known as primary cellulose fibrils or primary cellulose nanofibrils) embedded in a (primarily) hemicellulose matrix.

Nanocellulose materials have been the subject of a number of research studies in which the nanocellulose was used in the production of a composite material. For example, Abraham et al, Physicomechanical properties of nanocomposites based on cellulose nanofibre and natural rubber latex, Cellulose, (2013), 20:417-427, published 22 Nov. 2012, describes the use of NFCs having a diameter of 10 to 60 nm and obtained by the steam explosion of banana fibre as a reinforcing material mixed with natural rubber latex. This paper described loadings of NFCs added to the latex as including 2.5%, 5%, 7.5% and 10%. Table 2 of this paper shows that adding the NFCs to the natural rubber latex resulted in significant increases in elastic modulus (stiffness), and tensile strength and a decrease in elongation (strain) at break across all loadings of NFC.

Boufi et al, "Mechanical performance and transparency of nanocellulose reinforced polymer nanocomposites, Macromol. Mater. Eng. 2014, 299, pp 560-568, describes the use of two different types of NFC (one having 20 to 50 nm diameter, 200 to 1000 nm length, the other having 10 to 20 nm diameter, 200 to 1000 nm length) and two different types of CNC (one having 15 to 25 nm diameter, 150 to 250 nm length and the other having 15 to 25 nm diameter, 150-350 nm length) being dispersed in an acrylic latex at up to 15% loading. The nanocellulose materials were extracted from two different cellulosic sources, namely alfa and date palm trees. This paper found that a huge enhancement in modulus (stiffness) was observed in the polymer composite above the glass transition temperature (rubber state). Further, this paper states that the stiffness of the composites increases with an increase in the aspect ratio of the CNC.

Chaker et al, "Reinforcing potential of nanocellulose from non-woody plants," Polymer Composites—2013, describes the use of a number of NFCs derived from different sources (abaca, sisal, hemp, jute and flax) as fillers in an acrylic elastomer (a commercially available latex obtained by the copolymerisation of styrene (35% by weight) and butyl acrylate (65% by weight)). The NFCs had diameters in the range of 10 to 50 nm. The NFCs were described as comprising a bundle of primary nanofibrils of 3 to 5 nm diameter. The NFCs had a hemicellulose content that ranged from 6 to 20% weight. NFC loadings in the elastomer/NFC composite were up to 15% by weight. This paper observed a huge enhancement in modulus above the glass transition temperature of the elastomer. The paper states that this is a common effect seen in elastomer composites reinforced with nanocellulose. This paper also described composites including fibres with higher hemicellulose content as showing higher stiffness and tensile strengths compared to lower hemicellulose materials. FIG. 5 of this paper showed significantly increased stiffness and reduction in elongation to break on increasing NFC loadings.

US 2012/0232192 A1 discloses rubber composites incorporating organic fibres for improving the performance of automotive tyres. This document teaches the use of modified celluloses such as carboxymethyl cellulose (CMC) as an additive rather than unmodified celluloses, explaining that the presence of hydroxyl groups on unmodified cellulose promotes aggregation of the cellulose in water due to strong hydrogen bonding, resulting in poor dispersion in the rubber. The document goes on to describe modified cellulose particles that have an average diameter in the range 20 microns to 100 microns, teaching that particles with a diameter lower than 20 microns have poor dispersibility.

US 2013/0197132 A1 describes the incorporation of microfibrils of cellulose into elastomers including rubber latex. Cellulose microfibrils with diameters as low as 20 nm are disclosed in the examples however the document teaches against the use of unmodified cellulose as a reinforcing agent in rubber composites due to the poor compatibility of unmodified cellulose fibres with the rubber component. Specifically, poor adhesion at the rubber-cellulose interface is thought to contribute to increased friction and energy losses at the interface. The authors propose the addition of lignin to the cellulose fibres to modify the rubber-cellulose interface to increase adhesion at the interface.

Although increases in tensile strength and toughness are useful in a very large number of applications, in some uses, concomitant increases in elastic modulus or stiffness may not be so desirable. Reinforcing agents that have been previously used in elastomers to improve mechanical properties such as silica, carbon black, carbon nanotubes and graphene can provide an increase in tensile strength of an elastomer however due to their rigid nature, the incorporation of these materials also tends to increase the hardness and stiffness of a material and reduces the elongation to break. In many elastomer applications, increased stiffness and reduced elongation to break are detrimental to product performance such that the use of these reinforcers involves a fine balancing act and compromise between different performance features. For example, in the manufacture of condoms, it is desirable to use an elastomeric material that has good tensile strength and toughness but low elastic modulus (or high compliance). This combination of properties will result in a condom that is resistant to breakage but also allows for a close fit and improved feel or sensation. The use of elastomeric materials having undesirably highly elastic modulus is generally avoided in condom manufacture because those materials tend to decrease feel or sensitivity, and therefore cause consumer resistance.

Previous research studies focussed on using reinforcing agents to improve the mechanical properties of elastomers manufactured from latex-based systems such as natural rubber lattices and polyisoprene lattices have largely used the casting method to fabricate the elastomer composite products. Here, the reinforcing agent is added to the latex, followed by casting the mixture onto a surface and subsequently the carrier solvent is removed, leaving a composite of the elastomer and the reinforcing agent. However, commercial products such as condoms, gloves and catheter balloons that are made using latex-based elastomers are often not made by casting, but are instead made by dipping a shaped form or mould into latex followed by removal of the mould from the latex and then drying of the latex film deposited on the mould to yield a latex film or membrane of the desired shape. In such cases, the reinforcing agent that is present in the latex must not only provide improvements in the mechanical properties of the final product following dipping, but in order that the latex-reinforcing agent formulation is suitable for manufacture, the addition of the reinforcing agent must not destabilise the latex colloid so as to cause precipitation of the latex. Thus, in order to provide a manufacturable latex formulation that results in a suitably reinforced dipped product, the reinforcing agent must be well dispersed into the latex but not cause significant destabilisation. It is generally known that the extent of colloid destabilisation is approximately proportional to the amount of reinforcing agent added to the latex. Therefore, only very effective reinforcing agents will be successful in this application, that is, those reinforcing agents that can provide adequate mechanical reinforcement in the manufactured device but in quantities small enough so as not to destabilise the latex.

In other elastomer applications such as wear liners, seals and tyres similar technical requirements exist. In wear liners for example, elastomeric materials that exhibit high toughness and abrasion resistance are desired while still retaining the soft, elastic nature of the underlying rubber material. In tyres, softer compounds provide good road grip however these tend to wear more rapidly that harder compounds. Increasing the hardness of a tyre rubber compound reduces wear but at the expense of road grip. There is needed therefore, a soft rubber compound that provides good road grip while possessing good resistance to wear.

It will be clearly understood that, if a prior art publication is referred to herein, this reference does not constitute an admission that the publication forms part of the common general knowledge in the art in Australia or in any other country.

SUMMARY OF INVENTION

The present invention is directed to a composite material containing an elastomeric material and nanocellulose, which provides enhanced tensile strength and toughness when compared to the elastomeric material by itself but does not suffer from unduly increased elastic modulus or stiffness.

In a first aspect, the present invention provides a composite material comprising an elastomer and nanocellulose, the nanocellulose comprising a nanocellulose material derived from plants having C4 leaf anatomy.

In a second aspect, the present invention provides a composite material comprising an elastomer and nanocellulose, the nanocellulose comprising a nanocellulose material derived from a plant material having a lesser amount of lignin than hemicellulose.

In a third aspect, the present invention provides a composite material comprising an elastomer and nanocellulose, the nanocellulose having a hemicellulose content of from 25% to 50% by weight of the nanocellulose material.

In a fourth aspect, the present invention provides a composite material comprising an elastomer and nanocellulose, the nanocellulose comprising nanofibrils having a diameter of up to 5 nm, preferably a diameter within the range of 3-4 nm.

In a fifth aspect, the present invention provides a composite material comprising an elastomer and nanocellulose, the nanocellulose comprising nanocellulose material of plant origin comprising nanocellulose particles or fibres having an aspect ratio of at least 250.

In a sixth aspect, the present invention provides a composite material comprising an elastomer and nanocellulose, the composite material having a stiffness of not greater than 2.5 times the stiffness of the elastomer without the nanocellulose material being present.

The chemical functionality on the surface of a reinforcing agent such as nanocellulose is important both in the manufacture of nanocomposite elastomers and in determining the properties of the composite elastomers themselves. The manufacture of nanocomposite elastomers requires that the nanocellulose is well dispersed with the elastomer host polymer (such as latex particles or dissolved elastomer molecules in the case of dipping processes, or rubber molecules in the case of dry compounding approaches such as those used to manufacture tyres) and simultaneously does not contribute to any destabilisation or de-mixing of the elastomer formulation. This is especially challenging in the case of latex systems such as polyisoprene lattices or natural rubber lattices since good dispersion of a reinforcing agent in an elastomer, particularly nanomaterial reinforcing agents, typically requires significant amounts of energy to be applied (in a mixing process for example) and yet these formulations are often easily de-stabilised on the addition of even small amounts of energy. These latex systems, which are essentially negatively charged suspensions of rubber particles in an aqueous solvent are relatively easily destabilised on the addition of other chemical or particulate species, changes in pH, temperature, addition of significant amounts of mechanical energy and other factors. As such, an effective reinforcing agent must be easy to disperse in such formulations and not contribute to destabilisation of the manufacturing formulation. In the composite elastomer final product, chemical functionality on the surface of a reinforcing agent is important in determining the strength of the interface between the reinforcer and the elastomer and therefore the overall ability of the reinforcer to accommodate mechanical or other stresses placed on the elastomer. In their natural state, cellulosic materials including nanocellulose have a surface chemistry dominated by hydroxyl (OH) groups, as these are natural constituents of the polysaccharides that make up cellulose. At most pHs, these hydroxyl groups are negatively charged. The presence of a high density of hydroxyl groups on the surface of a nanocellulose reinforcing agent may provide a strong interface between the nanocellulose fibrils and the elastomer molecules through hydrogen bonding and other attractive forces. During the manufacturing process, the presence of a high density of negatively charged hydroxyl groups can also facilitate the formation of stable nanocellulose dispersions (since the nanocellulose particles repel each other via electrostatic interactions) and the formation of stable elastomer-nanocellulose formulations whether this is a suspension of nanocellulose in a solution of dissolved elastomer in a solvent or a latex colloidal dispersion where the negatively charged nanocellulose species repel each other and the negatively charged latex particles to allow a stable colloid to be maintained.

Some chemical treatments used by other groups to facilitate the production of cellulose nanofibrils from plant feedstocks result in modification of the surface functionality of the cellulose. For example, the TEMPO oxidation process results in a highly carboxylated cellulose nanofibrils surface. Since the nanocellulose used in the present invention may be manufactured without the use of harsh chemical agents, the hydroxylated surface of natural cellulose may be retained in the product cellulose nanofibrils. Alternatively, nanocellulose with surface chemical functional groups other than hydroxyl groups may be used to reinforce elastomers to manufacture the nanocomposite elastomers of the present invention and the selection of which chemical functional groups to use will be determined by factors such as the desired interaction and extent of reinforcing provided by the nanocellulose in a particular elastomer, the chemical composition of the elastomer molecules or surface functionality of latex particles, the solvent used in dipped formulations, desired interactions between the nanocellulose and compounding agents used and other factors. The various types of chemical functionality that can be achieved with nanocellulose materials and the methods for producing these functionalities are well known to those in the art and generally result from the nanocellulose manufacturing process or post-manufacture modification of nanocellulose. Such methods might include TEMPO oxidation, carboxymethylation, adsorption of surfactants, adsorption of macromolecules, esterification, acetylation, acylation, cationisation, sylation, carbamination, click chemistry, molecular grafting, polymer grafting or other methods well known in the art. Missoum et. al. (Materials, 2013, 6, 1745-1766) and Dufrense, Nanocellulose, December 2012, De Gruyter provide good summaries of methods available for the manufacture of nanocellulose with different surface chemical functionalities.

In a seventh aspect, the present invention provides a composite material comprising an elastomer and nanocellulose, the nanocellulose having a highly hydroxylated surface.

In one embodiment, the nanocellulose material comprises nanocellulose particles or fibres having an aspect ratio of at least 250.

Throughout this specification, the term "aspect ratio" is used to refer to the ratio determined from the maximum dimension of the nanocellulose particle divided by the minimum dimension of the nanocellulose particle. For nanocellulose fibers, the aspect ratio is determined by dividing the average length of the fibre by the average diameter of the fibre.

In one embodiment, the nanocellulose particles or fibres have an aspect ratio of between 250 to 10,000, or between 250 to 5000, or between 250 to 1000, or between 260 to 1000, or between 266 to 1000, or between 266 to 958.

The nanocellulose material preferably comprises cellulose nanocrystals (CNC) or nanofibrillated cellulose (NFC).

In some embodiments, the range of the aspect ratio of the nanocellulose particles or fibres has a lower limit of 250, or 266, or 280, or 300, or 400, or 500. In some embodiments, the upper range of the aspect ratio of the nanocellulose particles or fibres is 10,000, or 5000, or 4000, or 3000, or 2000, or 1000, or 958, or 800, or 700, or 600, or 550.

In many elastomer applications, an elastomer part may be required to perform under extreme stretch where extensions of 1000% (stretching ten times original length) or more are experienced. On stretching an elastomer part, the length extension is accompanied by a thinning of the cross section. In applications such as condoms and medical gloves where the elastomeric membrane is already thin (in the region of 30-50 microns for a condom), high extension can cause a reduction in membrane thickness down to just a few microns. In such cases, since the reinforcing materials are typically more rigid than the elastomer, membrane thickness reduction on extension is not accompanied by a proportional reduction in the thickness of a reinforcing material. As such, it is only feasible to use reinforcing materials that have a thickness substantially thinner than a few microns, otherwise the reinforcing material may cause distortions, reduced resistance to breakage and provide points for potential failure if the diameter of the reinforcing particle becomes significant compared to the thickness of the extended membrane. Under such circumstances it is advantageous to use reinforcing materials that have a diameter in the nanometre range. Many nanocellulose production processes produce nanocellulose products with a wide range of fibre diameters. While these prior art processes are capable of providing nanocellulose materials with diameters lower than 10 nm, they typically also produce fibres with much larger diameters. Since separation of smaller and larger fibres from a single batch is not easy or may not be economically feasible, it is advantageous to use nanocellulose that has been produced from a process where fibre diameters occupy a narrow size range in the nanometre range such that substantially all of the fibres produced have a diameter lower than 20 nm.

The nanocellulose particles or fibres may have a diameter of up to 20 nm, or up to 15 nm, or up to 10 nm, or up to 8 nm, or up to 6 nm, or up to 5 nm. In some embodiments, the nanocellulose particles or fibres comprise primary nanofibrils having a diameter of 3-4 nm. Preferably, the nanocellulose particles or fibres include essentially no particles or fibres having a diameter of greater than 20 nm.

It will be appreciated that the fibre diameter and aspect ratio values of any given sample of nanocellulose of the present invention will be composed by a distribution of values where the value quoted approximately represents an average of values for different fibres in a sample.

The nanocellulose particles or fibres may have a length that falls within the range of from 200 nm up to 10 μm.

In preferred embodiments, the nanocellulose material used in the present invention is of plant origin and therefore is derived from plant sources. In one embodiment, the nanocellulose of the present invention is derived from plant material in which the amount of hemicellulose in the plant material is greater than the amount of lignin in the plant material.

In one embodiment, the plant material is derived from a grass species having C4 anatomy. The present inventors believe that any plant materials from grasses having C4-anatomy can be used to produce the nanocellulose material (NFC or CNC) that is suitable for use in the present invention.

In one embodiment, the plant material is derived from a drought-tolerant grass species.

In one embodiment, the plant material is derived from arid grass species.

In one embodiment of the present invention, the plant material is derived from Australian native arid grass known as "*spinifex*". *Spinifex* (also known as 'porcupine' and 'hummock' grass) is the long-established common name for three genera which include *Triodia*, *Monodia*, and *Symplectrodia* (not to be confused with the grass genus *Spinifex* that is restricted to coastal dune systems in Australia). Hummock grassland communities in arid Australia are dominated by *spinifex* species of the genus '*Triodia*' There are 69 described species of *Triodia*, which are long-lived and deep rooted allowing root growth to penetrate through tens of metres under the ground. Of the 69 species, abundant species are two soft species called *T. pungens*, *T. shinzii* and two hard species *T. basedowii*, *T. longiceps*. *T. Pungens* has a typical composition of: cellulose (33%), hemicellulose (44%), lignin (23%) for the lignocellulosic components of the plant leaves.

Examples of other grasses with C4 leaf anatomy that may be used to form nanocellulose suitable for use in the present invention include *Digitaria sanguinalis* (L.) Scopoli, *Panicum coloratum* L. var. *makarikariense* Goossens, *Brachiaria brizantha* (Hochst. Ex A. Rich) Stapf, *D. violascens* Link, *P. dichotomiflorum* Michaux, *B. decumbens* Stapf *Echinochloa crusgalli* P. Beauv., *P. miliaceum* L., *B. humidicola* (Rendle) Schweick., *Paspalum distichum* L., *B. mutica* (Forsk.) Stapf, *Setaria glauca* (L.) P. Beauv, *Cynodon dactylon* (L.) Persoon, *Panicum maximum* Jacq., *S. viridis* (L.) P. Beauv, *Eleusine coracana* (L.) Gaertner, *Urochloa texana* (Buckley) Webster, *Sorghum sudanense* Stapf, *E. indica* (L.) Gaertner, *Spodiopogon cotulifer* (Thunb.) Hackel, *Eragrostis cilianensis* (Allioni) Vignolo-Lutati, *Chloris gayana* Kunth, *Eragrostis curvula*, *Leptochloa dubia*, *Muhlenbergia wrightii*, *E. ferruginea* (Thunb.) P. Beauv., *Sporobolus indicus* R. Br. var. *purpureo-suffusus* (Ohwi) T. Koyama, *Andropogon gerardii*, *Leptochloa chinensis* (L.) *Nees* and *Zoysia tenuifolia* Willd.

Since the *Triodia* grasses are grown under arid conditions, the present inventors believe that other arid grasses that grow in Australia and other parts of the world may also be used in the present invention. The most drought tolerant grass genera, in Australia, (though they need water in their first 1 or 2 years) include *Anigozanthos*, *Austrodanthonia*, *Austrostipa*, *Baloskion pallens*, *Baumea juncea*, *Bolboschoenus*, *Capillipedium*, *Carex bichenoviana*, *Carec gaudichaudiana*, *Carex appressa*, *C. tereticaulis*, *Caustis*, *Centrolepis*, *Chloris truncate*, *Chorizandra*, *Conostylis*, *Cymbopogon*, *Cyperus*, *Desmocladus flexuosa*, *Dichanthium sericeum*, *Dichelachne*, *Eragrostis*, *Eurychorda complanata*, *Evandra aristata*, *Ficinia nodosa*, *Gahnia*, *Gymnoschoenus sphaerocephalus*, *Hemarthria uncinata*, *Hypolaeana*, *Imperata cylindrical*, *Johnsonia*, *Joycea pallid*, *Juncus*, *Kingia australis*, *Lepidosperma*, *Lepironia articulate*, *Leptocarpus*, *Lomandra*, *Meeboldina*, *Mesomelaena*, *Neurachne alopecuroidea*, *Notodanthonia*, *Patersonia*, *Poa*, *Spinifex*, *Themedo triandra*, *Tremulina tremula*, *Triglochin*, *Triodia* and *Zanthorrhoea*. Arid grasses that grow in other parts of the world that may also be using the present invention include *Aristida pallens* (Wire grass), *Andropogon gerardii* (Big bluestem), *Bouteloua eriopoda* (Black grama), *Chloris roxburghiana* (Horsetail grass), *Themeda triandra* (Red grass), *Panicum virgatum* (Switch grass), *Pennisetum ciliaris* (Buffel grass), *Schizachyrium scoparium* (Little bluestem), *Sorghatrum nutans* (Indian grass) and *Stipa tenacissima* (Needle grass).

Other grasses that may also be used in the present invention include wheat straw, Esparto (provided by *Stipa tenacissima* and *Lygeum spartum*, both Poaceae family), Oyat (which is the French common name for *Ammophila arenaria*, also from the Poaceae family), *Miscanthus* (which has a similar composition as *T. Pungens*, with a typical composition being 37.7% cellulose, 37.3% hemicellulose, 25.1% lignin) and the plants that form tumbleweeds, including tumbleweed forming plants form the families Amaranthaceae and Chenopodiaceae), Amaryllidaceae, Apiaceae, Asphodelaceae, Asteraceae, Brassicaceae, Boraginaceae, Caryophyllaceae, Fabaceae, Lamiaceae and Poaceae.

Along with cellulose and lignin, hemicellulose is a key component of the various materials that constitute nanocellulose. It is believed that hemicellulose is likely distributed throughout the nanocellulose fibres both on the surface of the fibres and in between the primary (elementary) cellulose nanofibrils in cases where the nanocellulose fibres consist of bundles of primary cellulose nanofibrils. While cellulose is a more rigid crystalline material, hemicellulose is amorphous and consequently has weaker mechanical properties. With its distribution throughout the structure of nanocellulose, the inventors believe that hemicellulose may act to increase the flexibility of the nanocellulose, possibly acting as a plasticizer between the cellulose fibres and allowing individual cellulose fibres to creep and extend with respect to each other. While this might reduce the stiffness of the nanocellulose, it can potentially increase the fracture toughness of the nanocellulose (indeed, when the present inventors homogenise base-treated *spinifex*, which is an example of a suitable source of nanocellulose for use in the present invention, and compare that to other softwood or hardwood pulps, the inventors have found that the *spinifex* can be exposed to a much higher degree of mechanical energy without fibril breakage, which appears to be an indication of a much higher degree of nanocellulose toughness). The hemicellulose content of the nanocellulose is an important factor in determining the performance of the nanocellulose as a reinforcing agent in elastomers. The inventors have surprisingly found that elastomers reinforced with nanocellulose that has a high hemicellulose content have increased toughness compared to the unmodified elastomer but do not suffer from significant increases in stiffness or significant reduction in elongation to break. Without wishing to be bound by theory, the inventors believe that the use of high hemicellulose content nanocellulose provides a highly flexible reinforcer for elastomers where the hemicellulose not only facilitates slippage and extension between individual cellulose nanofibrils but between the nanocellulose and the elastomer molecules when tensile stress is applied. In this way, the high hemicellulose content enables a toughening of an elastomer without a significant increase in stiffness and to continue to provide this reinforcing even at high strains. In some embodiments of the present invention, the hemicellulose content of the nanocellulose is at least 30% by mass of the lignocellulosic components of the nanocellulose. Preferably, the hemicellulose content is from 30% to 55% w/w, or from 30 to 50% w/w, or from 36 to 48% w/w, or from 40 to 48% w/w or from 42 to 47% w/w, or any intermediate range within the ranges set out above. These high hemicellulose contents may be achieved by any means, including but not limited to, using plant feedstocks that are naturally high in hemicellulose and subsequent processing to produce nanocellulose that retains a high hemicellulose content, or alternatively, using a nanocellulose material that has lower hemicellulose content and mixing it with a separately produced hemicellulose material to give a mixture that provides a high hemicellulose content nanocellulose.

In some embodiments the nanocellulose comprises a nanocellulose material of plant origin comprising nanocellulose particles or fibres derived from a plant material having a hemicellulose content of 30% or higher (w/w). In other embodiments, the plant material has a hemicellulose content of from 30 to 55% w/w, or from 30 to 50% w/w, or from 36 to 48% w/w, or from 40 to 48% w/w or from 42 to 47% w/w, or any intermediate range within the ranges set out above.

Plant materials are composed of many different substances including waxes and resins, ash and lignocellulosic components. Lignocellulosic components are the major components of plant matter and comprise lignin, cellulose and hemicellulose. Throughout this specification, the hemicellulose content of materials is discussed in percentage terms. In all cases, the hemicellulose content is quoted as a mass percentage of the total mass of the lignocellulosic components only of the relevant material.

Hemicellulose content and the content of other lignocellulosic components was measured by chemical analysis. Specifically, TAPPI standard methods were used to characterize the components present in *spinifex* grass samples before and after pulping. Initially, *spinifex* water-washed grass and fibre samples were ground to 60 mesh fibre size using a small Wiley mill. Then the ground fibre samples were extracted with ethanol in a Soxhlet apparatus (Tecator Soxtec System Model HT 1043, from Foss, Denmark) for one hour followed by rinsing with water for another hour. The total lignin content was determined using the standard methods (TAPPI, Acid-insoluble lignin in wood and pulp, modified method based on Test Method T-222 om-88, 1988; TAPPI, Acid-soluble lignin in wood and pulp, Useful Method UM-250, 1991). Monomeric sugars also were determined by ion chromatography according to the reference Pettersen, R. C.; Schwandt, V. H. *Journal of wood chemistry and technology* 1991, 11, (4), 495-501.

In some embodiments, the amount of nanocellulose that is present in the composite may vary from 0.05% wt to 25% wt (calculated as a weight percentage of the total weight of the nanocellulose and elastomer components, that is, excluding other chemicals added during compounding such as vulcanising agents, surfactants and accelerators). In some embodiments, the amount of nanocellulose that is present in the composite may vary from 0.05% wt to 25% wt, or from 0.2% wt to 20% wt, or from 0.3% wt to 15% wt, or from 0.5% wt to 10% wt, or from 0.5% wt to 7.5% wt, or from 0.5% wt to 7% wt, or from 0.5% wt to 5% wt, or from 0.5% wt to 2.5% wt, or about 0.5% wt, or about 1% wt. In some embodiments, including embodiments suitable for use in condom manufacture, the composite material will contain less than 5% wt nanocellulose and may contain between 0.1% to 1% wt nanocellulose or between 0.05 wt % and 0.5 wt. % or from 0.05 to 0.5% wt or from 0.1 to 0.4% wt nanocellulose.

The nanocellulose is preferably well dispersed in the composite. In some embodiments, the nanocellulose is dispersed by mixing the nanocellulose with particles of the elastomer or by mixing the nanocellulose with a dispersion or emulsion containing the elastomer. In other embodiments, the elastomer is prepared by reacting two or more monomers together and the nanocellulose may be mixed with one or more of the monomers or mixed into the mixture of monomers so that the nanocellulose is present during the reactions that take place to form the elastomer. In other embodiments, the nanocellulose is dispersed in a solution comprising an elastomer dissolved in an appropriate solvent. In the case of dipped formulations wherein the elastomer formulation is a latex dispersion, the nanocellulose may be added to the latex dispersion as a powder or as a dispersion in an appropriate solvent or liquid. Where compounding agents such as curatives, accelerators, stabilisers or vulcanising agents are added to the latex formulation, the nanocellulose may be mixed with latex first, followed by addition of the compounding agents or the nanocellulose may be mixed with the compounding agents followed by addition of this mixture to the latex. In dipped formulations wherein the elastomer is dissolved in appropriate solvent, the nanocellulose may be added to the elastomer solution as a dry powder or suspended in an appropriate solvent prior to mixing with the elastomer solution.

In other embodiments, the nanocellulose may be dispersed in an elastomer or mixture of elastomers wherein the elastomer is used in the process in solid form. In these types of processes, for example in the manufacture of automotive tyres, solid elastomer is mixed with compounding agents including vulcanising agents, curatives, accelerators, dispersants or other compounding agents known to those skilled in the art in a two-roll mill or other processing equipment to develop the compound prior to vulcanisation. In such processes, the nanocomposite elastomer of the present invention may be manufactured by addition of the nanocellulose to the formulation at any stage in the process prior to vulcanisation. In one case, the nanocellulose may be combined with the compounding agents prior to their mixing with the elastomer, or the nanocellulose may be mixed into the formulation at the same time as the compounding agent are added to the elastomer. Alternatively, the nanocellulose may be added to the elastomer prior to addition of the compounding agents. Mixing of the elastomer with the nanocellulose may be done by mixing the nanocellulose in powder form with the elastomer of the nanocellulose may be added to the elastomer as a masterbatch. In the case that a masterbatch strategy is used, the nanocellulose may be pre-dispersed into a relatively small quantity of elastomer or another host material that can be added to the main elastomer during the production process. Suitable materials to act as a host in masterbatching as well known to those skilled in the art and include, but are not limited to EVA, waxes, other elastomers of the same elastomer as the main elastomer, or combinations of these.

In one embodiment, the elastomer comprises natural rubber. Natural rubber is produced in the form of a latex from the rubber tree (*Hevea Brasiliensis*) and is then used to manufacture rubber goods in the form of a latex (such as in the case of surgical gloves, catheter balloons or condoms) or in a dried solid block form which is subsequently compounded with other materials to manufacture a finished product (such as in the case of automotive tyres). In this embodiment, the natural rubber may comprise a latex or be in solid form. In the case of a latex, the nanocellulose maybe mixed into the rubber dispersion at any point prior to vulcanisation and the composite formed as the natural rubber latex dries. The mixture of the nanocellulose and the elastomeric dispersion may be formed by mixing the two components together through a micronizer or homogenizer, or by mixing the nanocellulose in the dispersion using known mixing apparatus, such as mechanical stirrers, mills, ultrasonic stirrers, Silverson mixers or magnetic stirrers. In the case of natural rubber latex, the use of nanocellulose with a high hemicellulose content is beneficial for good dispersion of the nanocellulose in the latex since the hemicellulose imparts a negative charge on the nanocellulose, allowing it repel the negatively charged natural rubber latex and avoid coagulation. In cases where a rubber product is manufactured from solid rubber block form, the nanocellulose may be incorporated into the natural rubber while still in latex form prior to drying or it may be introduced at the compounding step along with other materials incorporated during compounding.

In another embodiment, the elastomer comprises a polyurethane. Polyurethanes are elastomers that are formed using isocyanate monomers and polyol monomers. In this embodiment, the nanocellulose may be mixed with one of the monomers that is added to the reaction mixture used to make the polyurethane. Alternatively, the mixture of monomers may be formed and the nanocellulose may be mixed into the reaction mixture before it has set or fully reacted. The polyurethane may comprise a thermoplastic polyurethane. As the nanocellulose contains hydroxyl groups that may also react with the isocyanate, a small excess of isocyanate could be added to the reaction mixture. Here, the hydroxyl groups on the surface of the nanocellulose may act in a similar way as a polyol such that following polymerisation, the nanocellulose is covalently bound into the structure of the polyurethane. Alternatively, the polyurethane-based nanocomposite elastomer may be fabricated using a dispersion of nanocellulose in polyurethane dissolved in a solvent or it may be manufactured from a dispersion of polyurethane particles in an appropriate solvent.

Other elastomeric materials may also be used in the present invention, including polyisoprene (synthetic natural rubber), polybutadiene, polychloroprene, butyl rubber, styrene-butadiene rubber, nitrile rubber, hydrogentated nitrile rubber (HNBR), ethylene propylene rubber, ethylene propylene diene rubber (EPDM), chlorosulphonated polyethylene (CSM), chlorinated polyethylene, polysulphide rubber, ethylene acrylic rubber, fluorocarbon rubber, polytetrafluoroethylene-propylene, epichlorohydrin rubber, polyacrylic rubber, silicone rubber, fluorosilicone rubber, polyphosphazene rubber, polyoctenylene, polypropylene oxide rubber, polynorbornene, polyether block amides, EVA rubber, styrenic block copolymers such as SEBS (styrene, ethylene-co-butylene, styrene blocks), SEPS (styrene, ethylene-co-propylene, styrene blocks), SIS (styrene, isoprene, styrene blocks) or other segmented elastomers such as copolyester thermoplastic elastomers (TPEs). Any combination of the above elastomers may also be used. Other elastomeric materials may also be used in the present invention. Many synthetic rubbers are produced as an organic solution where the elastomer polymers are dispersed in an organic solvent. These organic solutions may be subsequently coagulated and dried into solid rubber, or converted into a latex dispersion by exchanging the organic solvent with water so that an emulsion is formed. Finished products may then be fabricated from these forms of rubber. In the case of tyres for example, solid rubber block may be compounded with other chemical agents and then this compound may be formed into the desired tyre shape prior to vulcanisation. In the case of condoms for example, a latex dispersion may be compounded with other chemical agents and this mixture may then be used to form a condom shaped device by dip coating, prior to vulcanisation. The nanocellulose may be incorporated into synthetic elastomers at any point in the manufacture of the elastomers or their subsequent processing to produce a finished part. For example, the nanocellulose may be incorporated during the polymerisation of the elastomers so that it mixes with the monomers and the elastomer polymers are polymerised around the nanocellulose. Alternatively, following completion of polymerisation, the nanocellulose can be dispersed into the organic solvent/elastomer mixture that is present on completion of polymerisation and before the solvent is removed to form a solid elastomer block or solvent exchange is carried out to form a latex suspension. By following this approach, excellent dispersion of the nanocellulose in the elastomer can be achieved since the mixing process occurs at a point in the process when the elastomer is in a dissolved form and highly mobile. Subsequent removal of the solvent to form a solid elastomer block or solvent exchange to form a latex results in an elastomer containing well dispersed nanocellulose reinforcement. Alternatively, in the case of solid elastomer blocks, a solid elastomer block may be re-dissolved in an appropriate organic solvent and then the nanocellulose may be added followed by removal of the organic solvent. This enables incorporation of the nanocellulose into solid rubber blocks at points in the supply downstream from where the initial rubber block is formed. Alternatively, nanocellulose may be added into an already formed latex dispersion. This may provide for reinforcing between the individual rubber particles. The nanocellulose may be incorporated as a masterbatch. The nanocellulose may also be incorporated into the elastomer at the point of compounding where solid elastomer is combined with other agents such as vulcanising agents, silica particles and carbon black. As is well known in the art, the good performance of nanomaterials as reinforcing agents in polymer composites requires good dispersion of the nanomaterial throughout the polymer. In general, this is more easily achieved when the rubber is present in a low viscosity form or is finely divided such as when it is in a dissolved state in a solvent. Adequate dispersion may become more difficult to achieve during compounding steps where the nanocellulose is being dispersed into a solid rubber host material, but those skilled in the art can still accomplish very good results by the high shear "masterbatching" of concentrates and subsequent "let-down" of these concentrates in processing equipment typically used in rubber compounding or thermoplastic elastomer melt processing.

Furthermore, the elastomer composite of the present invention may include various additives that are used by those skilled in the art such as zinc oxide, surfactants including but not limited to stearates, anti-oxidants, waxes, vulcanising agents and vulcanising accelerators.

In other embodiments, the nanocellulose is formed by treating plant material. In some embodiments, the elastomer or precursor(s) to the elastomer may be added to the plant material during processing of the plant material to form the nanocellulose. For example, the nanocellulose may be formed from plant material by a process that includes milling the plant material or passing it through a high pressure homogeniser or a micronizer (jet mill). The elastomer or a precursor thereof may be added to the plant material so that the elastomer or precursor thereof is present during milling or homogenisation or micronization.

The elastomer may be a non-vulcanised elastomer. In other embodiments, the elastomer may be a vulcanised elastomer. Vulcanisation may occur with the nanocellulose being present in the elastomer.

In condom and surgical glove applications, the use of nanocellulose as a reinforcing material in an elastomer may improve the toughness and tensile strength of the elastomer and so provide more reliable products less prone to breakage, without a significant increase in elastomer stiffness that could lead to reduced sensation for the user in these applications. This improved reliability is especially important in condom applications where a manufacturer may wish to produce a condom with an exceptionally thin elastomer membrane to improve sensation. In such devices, reliability is significantly reduced due to the use of a thin membrane which is mechanically less robust than thicker membranes. The use of nanocellulose as a reinforcing agent can thus enable high reliability, thin elastomer membranes for use in condoms.

Another benefit for condom and surgical glove applications may be improved viral barrier performance in products utilising nanocellulose reinforcement. Products derived from latex such as surgical gloves and condoms are porous in nature and consequently do not offer a complete barrier to virus penetration. Since nanocellulose is composed of high aspect ratio fibres with a small fibre diameter, even the small concentrations of nanocellulose in an elastomer provided by some embodiments of the present invention can enable the formation of nanocellulose fibre networks in the elastomer that can act as a barrier to virus penetration through an elastomer membrane. The high aspect ratio of the fibres ensures a large number of fibre to fibre interconnections for network formation while the small fibre diameter means that the "holes" in the network may be suitably small to trap virus particles as they try to traverse the latex membrane.

Another problem observed in some elastomer applications, particularly surgical gloves and condoms is poor resistance of elastomers to oils. Exposure of some elastomers, especially natural rubber and synthetic rubber (polyisoprene), to oils can cause swelling of the material and significantly reduce the mechanical properties, leading to breakage. In condom applications, exposure to oil often occurs when a user inadvertently uses oil-based lubricants. By providing a reinforcing matrix that is not susceptible to breakdown by oils, nanocellulose reinforcing of elastomers in these applications can provide resistance to swelling of the elastomer and reduce degradation of mechanical properties on exposure to oils, providing a more reliable and robust product.

The manufacture of many rubber products requires handling of a part during manufacture prior to vulcanisation of the part. While the vulcanisation process increases the strength of a part due to cross-linking of the elastomer molecules, unvulcanised parts can have relatively poor strength such that handling these during manufacture is difficult and can result in damage to the part, manufacturing yield losses or decreased product reliability during service. This is particularly the case for parts such as medical gloves and condoms where the part contains thin membranes that are susceptible to breakage while being handled prior to vulcanisation. An advantage of the present invention is that the reinforcing effect provided by the nanocellulose fibres is not only observed in the final manufactured part but also provides reinforcement of a part during the manufacturing process such that the rate of defect formation in parts, particularly fragile parts such as condoms and medical gloves, can be reduced during manufacture to provide lower yield losses and more reliable operation in service.

The present invention also extends to articles manufactured from the elastomer composite. A wide range of elastomeric articles may be manufactured using the elastomer composition of the present invention, including condoms, gloves, catheter balloons, vehicle tyres, components for shoes, conveyor belts, wear liners, components for furniture (such as armrests), suspension bushes, blades for windscreen wipers and the like.

In one embodiment, the present invention consists in a dipped article such as a condom, glove or catheter balloon wherein nanocellulose is used as a reinforcing agent. Dipped articles are typically manufactured using either latex dispersions or solutions of elastomers dissolved in an appropriate solvent. The elastomer system used may be either pre-vulcanised or post-vulcanised. In the case of condoms, these are typically manufactured using a straight dipping process wherein a glass mould or former is lowered into a latex suspension, removed, then dried and a second dipping step is carried out in order to deposit a second layer of elastomer. This double dipping process reduces the number of pin holes in the condom and builds up the thickness of the elastomer membrane to a suitable level. In the case of gloves, coagulant dipping is typically used wherein a mould or former is first immersed into a coagulate suspension or solution (typically based on a calcium salt solution), dried and then dipped into a latex suspension whereupon the latex is deposited onto the mould. The dried coagulant layer on the mould causes local precipitation (destabilisation) of the elastomer colloid close to the mould surface and deposition of the elastomer onto the mould. These processes are well understood by those skilled in the art. The dipped articles of the present invention may be manufactured using any of the processes described herein or known to a skilled person.

A widely shared objective in condom applications is the desire to develop ultra-thin devices that have high strength, and therefore are reliable and resist breakage during use, but which are soft enough to provide good tactility and sensitivity during use. In general, and as with many materials, the strength of condom elastomer membranes decreases as the thickness of the membrane decreases. Therefore, thinning of condom elastomer membranes to produce ultra-thin devices is typically accompanied by a reduction in the strength and reliability of the material. In order that ultra-thin, yet strong condoms can be enabled, the mechanical properties of the elastomer used requires fundamental improvement. The international standard ISO4074:2002 describes two key tests for measuring condom strength, namely, the tensile test which measures the tensile strength (tensile stress) at break as a key figure of merit, and the air burst test wherein a condom is inflated with air and the pressure at burst is measured. Tensile strength figures derived from the tensile test are independent of condom thickness so allow reliable comparison between condoms of different thickness. Air burst pressure figures however (expressed in kPa) do not consider condom thickness. Therefore, a useful figure of merit to use in comparing air burst test data is the air burst pressure normalised for thickness that can be obtained by dividing air burst pressure (in units of kPa) by the thickness of the condom elastomer membrane (in units of microns). This "normalised air burst pressure" figure has the units of kPa/μm Commercial ultra-thin condom devices typically have tensile strength values of up to 31 MPa with normalised air burst pressure values of 0.025 kPa/μm to 0.036 kPa/μm. By making fundamental improvements to the mechanical properties of the elastomers used in condom manufacture by using nanocellulose reinforcing agents as described herein, the inventors of the present invention have been able to increase the mechanical performance of natural rubber latex and polyisoprene elastomers used in condom manufacture. Specifically, tensile strength values of greater than 31 MPa and normalised air burst pressure values greater than 0.036 kPa/μm can be achieved. In one embodiment, the present invention consists in a condom made from natural rubber latex or polyisoprene with tensile strength greater than 31 MPa, or greater than 35 MPa or greater than 40 MPa or greater than 45 MPa. The condom may have a maximum tensile strength of up to 60 Mpa, or up to 55 Mpa, or up to 50 MPa, or up to 45 Mpa. In another embodiment, the present invention consists in a condom made from natural rubber latex or polyisoprene with a normalised air burst pressure of greater than 0.036 kPa/μm or greater than 0.040 kPa/μm or greater than 0.045 kPa/μm or greater than 0.050 kPa/μm. The condom may have a maximum normalised air burst pressure of up to 0.007 kPa/μm, or up to 0.065 kPa/μm, or up to 0.060 kPa/μm, or up to 0.055 kPa/μm.

Many strategies to improve the strength of elastomers used in condom applications are successful but often result in significant increases in the modulus of the material, or stiffness, such that softness of the elastomer is sacrificed in order to gain strength. By using the soft, flexible, but tough nanocellulose reinforcing agents of the present invention, it is possible to develop ultra-thin condoms that have high tensile strength and/or high normalised air burst pressure but which simultaneously retain a soft feel. In order to quantify softness herein, we use a figure of merit derived from the ISO4074:2002 tensile test that is the tensile stress of an elastomer at 500% extension. Accordingly, one embodiment of the present invention consists in a condom made from natural rubber latex or polyisoprene with tensile strength greater than 31 MPa, or greater than 35 MPa or greater than 40 MPa or greater than 45 MPa or a normalised air burst pressure of greater than 0.036 kPa/μm or greater than 0.040 kPa/μm or greater than 0.045 kPa/μm or greater than 0.050 kPa/μm and a tensile stress at 500% extension of lower than 10 MPa or lower than 8 MPa or lower than 6 MPa or lower than 4 MPa or lower than 2 MPa or lower than 1.5 MPa or lower than 1 MPa. The condoms may have maximum tensile stress and normalised air burst pressure as set out in the preceding paragraph.

Condoms of the present invention may be of any thickness. The increased strength of the nanocomposite elastomers of the present invention may be used to manufacture condoms with thickness similar to that of conventional condoms (typically in the range 50-90 microns for natural rubber latex or polyisoprene condoms) but with improved strength and reliability, or alternatively, the nanocomposite elastomers may be used to manufacture ultra-thin condoms that are thinner than or of equivalent thickness to existing ultra-thin devices (these typically have thicknesses in the range 36-50 microns), but which have improved strength or reliability over these ultra-thin products. Condoms of the present invention may have thickness of less than 45 μm or less than 40 μm or less than 35 μm or less than 30 μm or less than 25 μm in the case that these are made using natural rubber latex or polyisoprene, or less than 10 μm in the case that they are made using polyurethane.

In a further aspect, the present invention provides a method for producing an article from a composite material as described herein, the method comprising forming a mixture of the nanocellulose and a suspension or solution of elastomeric material, dipping a mould or a former into the mixture, removing the mould or the former from the mixture such that an adherent layer of the mixture is formed on a surface of the mould or the former and allowing the adherent layer of the mixture to dry or set.

The method may comprise a further step of dipping the mould or former back into the mixture one or more further times to form additional layers of adherent mixture. The additional layers of adherent mixture may form on an underlying layer of adherent mixture. The mould or former may be dipped back into the mixture after a previous adherent layer has dried or set. The nanocellulose may be homogenously dispersed or mixed through the mixture.

The method may comprise a further step of removing the article from the mould or former.

In one embodiment of the method, the nanocellulose may have a hydroxylated surface. In other embodiments of the method, the surface of the nanocellulose may be modified to attach functional groups to the surface of the nanocellulose. The surface of the nanocellulose may be modified by TEMPO oxidation, carboxymethylation, adsorption of surfactants, adsorption of macromolecules, esterification, acetylation, acylation, cationisation, silylation, carbamination, click chemistry, molecular grafting, polymer grafting.

In tests conducted by the present applicants, articles (in this case, condoms) were made by deep coating a former into a mixture comprising an elastomer suspension or solution and nanocellulose. It was surprisingly found that pending the nanocellulose to the elastomer suspension or solution did not cause precipitation or flocculation of elastomer from the suspension or solution.

In the description of the present invention, the term "elastomer" and "rubber" may be used interchangeably.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

DESCRIPTION OF EMBODIMENTS

It will be appreciated that the following examples have been provided for the purpose of illustrating preferred embodiments of the present invention. Therefore, it would be understood that the present invention should not be considered to be limited solely to the features as described in the examples.

Example 1

Nanocomposites were prepared via reactive extrusion of a stable, very dry (<300 ppm water) PTMEG 1000 polyol-CNC suspension with dimethyl diphenyl diisocyanate (MDI) and 1,4-butanediol (BDO). Table 1 summarizes the amount of each components used for making blank TPU and its nanocomposites with CNC (CNC was obtained from acid hydrolysis of *Spinifex* pulp using 40% (v/v) sulphuric acid for 3 hours at 45° C.).

Nanocellulose was present in an amount of 0.5% wt by weight of the composite (see X5 in table 1 above. X1 being the unfilled control).

In order to reduce the effect of moisture, PTMEG and stable PTMEG/CNC suspensions were dried using thin/wiped film evaporator (VTA, Niederwinkling, Germany) achieving water contents of below 300 ppm, and purged with nitrogen gas before storage in an air-tight bottle until required for reactive extrusion. The dispersion of *spinifex* CNC in PTMEG was prepared using 0.83% (w/w) CNC using a proprietary mixing process. Before doing the extrusion, PTMEG and MDI both were melted at 55° C. overnight and the chain extender (BDO) was dried using molecular sieve in a bottle, then all of these precursors were sealed with an air-tight lid and nitrogen gas purge.

Composition used for producing TPU based on blank PTMEG 1000

| Hard segment ratio | Isocyanate ratio | Stoichiometry | Polyol (wt %) | MDI (wt %) | BDO (wt %) |
|---|---|---|---|---|---|
| 0.44 | 1 | 1 | 56 | 36.06 | 7.94 |

Figure 1:
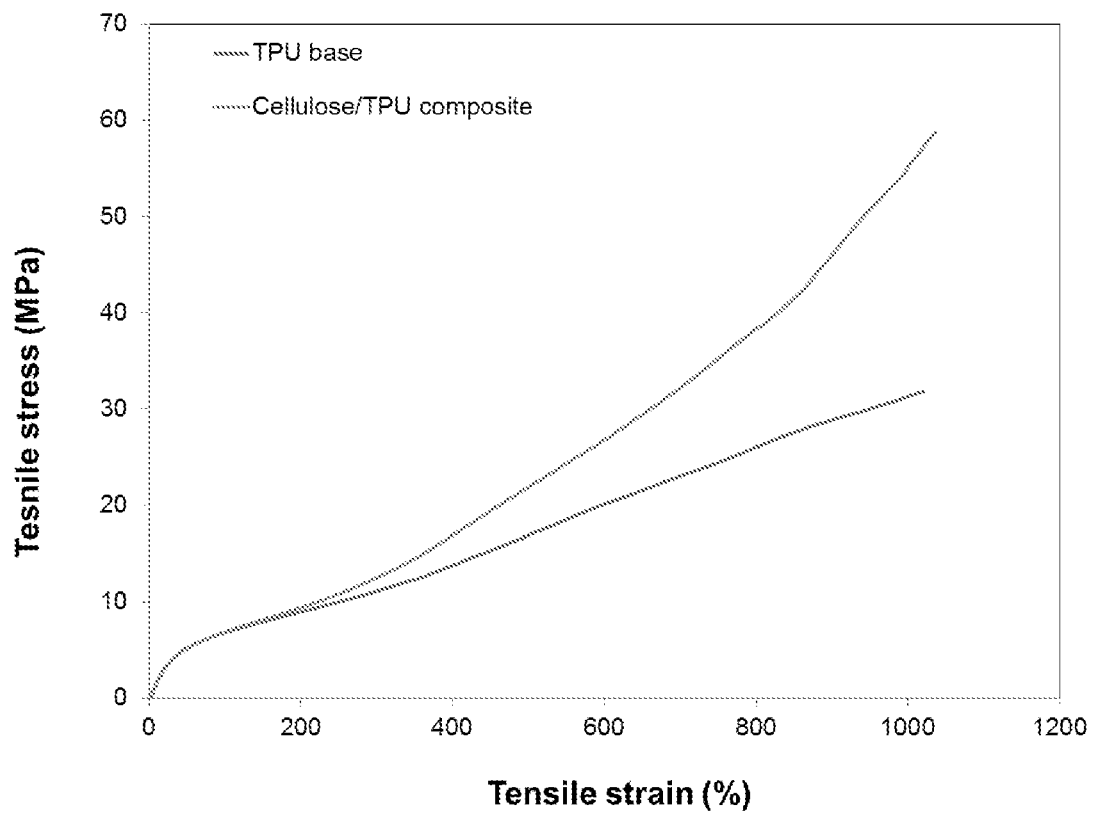
FIG. 1 shows a graph of tensile stress vs tensile strain for a polyurethane rubber having (a) no nanocellulose added and (b) 0.5% wt nanocellulose added.

FIG. 1 shows a graph of tensile stress vs tensile strain for the base TPU (with no nanocellulose), which is the lower curve in FIG. 1 and for the nanocellulose/TPU composite material, which is the upper curve in FIG. 1. As can be seen from FIG. 1, there was no increase in stiffness of the composite material, when compared to the base TPU, at low strain. A 45% increase in toughness was observed. There was no reduction in elongation to break.

TABLE 1

| Sample | Polyol type | CNC content (%) | Isocyanate index | Hard segment ratio | Stoichiometry | Polyol flow rate (g/h) |
|---|---|---|---|---|---|---|
| X1 | PTMEG1000 | — | 1 | 0.44 | 1 | 1797.6 |
| X2 | PTMEG1000 + CNC | 0.465 | 1 | 0.44 | 1 | 1812.5 |
| X3 | PTMEG1000 + CNC | 0.465 | 1 | 0.44 | 1.01 | 1812.5 |
| X4 | PTMEG1000 + CNC | 0.465 | 1 | 0.44 | 1.02 | 1812.5 |
| X5 | PTMEG1000 + CNC | 0.465 | 1 | 0.44 | 1.03 | 1812.5 |

| Sample | MDI flow rate (g/h) | BDO flow rate (g/min) | Torque (%) | Die pressure (bar) |
|---|---|---|---|---|
| X1 | 1157.6 | 254.8 | 26-27 | 15 |
| X2 | 1157.6 | 254.8 | 26 | 16 |
| X3 | 1169.1 | 254.8 | 30-31 | 21-22 |
| X4 | 1180.7 | 254.8 | 39-40 | 32-33 |
| X5 | 1192.3 | 254.8 | 43 | 37-38 |

| Sample | Young's Modulus (MPa) | Tensile strain (go) | Tensile stress (MPa) | Work at fracture (MJ m-3) |
|---|---|---|---|---|
| X1 | 14.5 ± 1.2 | 1124 ± 31 | 41 ± 3 | 237 ± 10 |
| X2 | 16.6 ± 0.3 | 1115 ± 41 | 43 ± 1 | 237 ± 6 |
| X3 | 14.5 ± 0.4 | 1098 ± 21 | 48 ± 1.2 | 257 ± 6 |
| X4 | 14.5 ± 0.6 | 1023 ± 11 | 54 ± 2 | 250 ± 9 |
| X5 | 16 ± 0.7 | 1012 ± 25 | 59 ± 3.2 | 256 ± 14 |

Example 2

In example 2, a composite material was produced from nanofibrillated cellulose and natural rubber latex (non-vulcanised). Nanocellulose was present in an amount of 1% wt of the composite.

The nanocellulose suspension (0.3-1%) was obtained via high-pressure homogenisation of *spinifex* pulp (*T. Pungens*) fibre. The nanocellulose used had a hemicellulose content of 42% w/w and a fibre diameter of 3.5 nm. Prior to mixing, the pre-vulcanized rubber latex (Gedeo concentrated mould making formula, Pebeo, France) was diluted to 20-50 mg/mL (on dry weight basis) depending on final composition (0.25, 0.5 and 1 wt. %). Both the suspensions were mixed together by magnetic stirring for 2-3 h, homogenised (using a hand held rotor-stator homogeniser) for 1-2 minutes and allowed to gently stir for another hour to degas. After degassing, the homogeneous mixture was cast onto Teflon petri-dishes, dried at 40° C. for 12 h-50 h (depending on nanocellulose content and volume) to obtain control and nanocomposite films.

Figure 2:
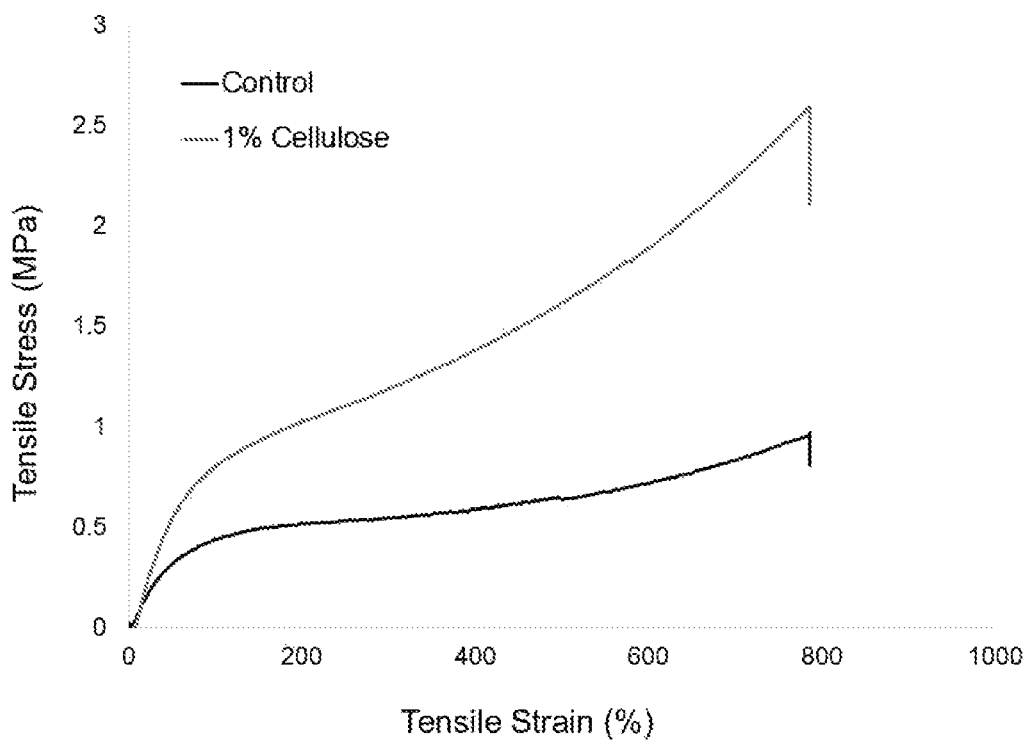
FIG. 2 shows a graph of tensile stress vs tensile strain for a natural latex having (a) no nanocellulose added and (b) 1.0% wt nanocellulose added.

FIG. 2 shows a graph of tensile stress vs tensile strain for the base natural rubber (with no nanocellulose), which is the lower curve in FIG. 2 and for the nanocellulose/natural rubber composite material, which is the upper curve in FIG. 2. FIG. 2 shows that although there was some increase in stiffness at low strain, this increase is not significant. However, toughness increased by 125%. There was no reduction in elongation to break.

Example 3: Nanocellulose Reinforced Synthetic Rubber (Polyisoprene)

A composite of synthetic rubber (Cariflex IR401 polyisoprene latex in water) and nanocellulose (NFC with 42 wt. % hemicellulose content and 3-4 nm fibre diameter) was fabricated where the NFC was present at a loading of 0.53 wt. % (dry NFC mass) and rubber made up 99.47 wt. % (dry rubber mass) of the total nanocellulose plus rubber dry mass. The NFC was well dispersed as a 3.5% w/v aqueous dispersion and this was added to the Cariflex IR401 latex dispersion which had a solids content of 66% wt. Addition was done at room temperature and the mixture was stirred gently for 1 hour after addition. Sulfur (0.6% wt. of total solids mass), ZnO (0.2% wt. of total solids mass) and zinc diethyl dithiocarbamate (ZDEC, 0.5% wt.) were then added slowly to the dispersion to avoid shocking the latex. After all additions were completed, stirring was continued for 1 hour. After that stirring was stopped and stirred just once a day for 30 min. The latex was kept for 48 hours at room temperature before casting. The composite was cast into a glass petri dish and was cured for 20 minutes at 125-130° C. in casting oven under the flow of nitrogen.

Example 4: Nanocellulose Reinforced Nitrile Butadiene Rubber (NBR)

A composite of nitrile butadiene rubber and nanocellulose (NFC with 42 wt. % hemicellulose content and 3-4 nm fibre diameter) was fabricated where the NFC was present at a loading of 6.5% wt. (dry NFC mass) and rubber made up 93.5% wt. (dry rubber mass) of the total nanocellulose plus rubber dry mass.

5 g of solid NBR was dissolved in 100 mL of dimethylformamide (DMF). NFC was then dispersed in a separate quantity of DMF and 10 mL of a 3.5 w/v % NFC in DMF dispersion was added to the NBR/DMF dispersion and stirred overnight at room temperature. The mixture was cast onto a glass surface, allowed to dry and curing was then done at 45° C. in casting oven under the flow of nitrogen for 48 hours.

Various methods for modifying the nanocellulose surface chemical functionality prior to incorporation with an elastomer, as specified in examples 5 to 10 set out below.

Example 5: Sodium Hydroxide Treated (Delignified) NFC (NFC Produced After Delignification Process)

*Triodia pungens* water-washed ground grass was treated with a 2% (w/v) sodium hydroxide solution at 80° C. for 2 hours followed by rinsing with hot water (60° C.). The alkali treated fibres contained 31% (w/w) cellulose, 43% (w/w) hemicellulose and 26% (w/w) lignin. An aqueous dispersion of these fibres with 0.5% (w/v) concentration, was then passed through a high pressure homogeniser (Panda 2 K NS1001L, GEA Niro Soavi S.p.A, Italy) at a pressure of 700 bar for 2, 4 or 8 passes.

Example 6: Bleached NFC

Alkali treated (delignified) fibres were bleached twice using a 1% (w/v) aqueous solution of sodium chlorite at 70° C. for 1 h with a 30:1 solvent to fibre ratio at pH 4 (pH adjusted with addition of a few drops of glacial acetic acid). The bleached pulp contained 55% (w/w) cellulose, 42% (w/w) hemicellulose and 3% (w/w) lignin. A 3 wt % dispersion of bleached pulp in water was then passed through high pressure homogeniser (Panda 2 K NS1001L, GEA Niro Soavi S.p.A, Italy) at 700 bar pressure two times. The average diameter of individual nanofibres and bundles of nanofibres were 4.5±1.5 nm and 9.7±7.1 nm, respectively.

Example 7: NFC Obtained After Carboxymethyl Treatment of Both Sodium Hydroxide Treated (Delignified) and Bleached Fibres Both delignified and bleached fibres were pretreated with the carboxymethylation procedure. Briefly, about 5 g of each fibre sample was solvent exchanged with ethanol using a centrifuge for 10 min with 5 repeats. Then fibres were impregnated in a 2% (w/v) solution of monochloroacetic acid in 45 mL of isopropanol for 30 minutes followed by addition to this mixture of a 2.5% sodium hydroxide solution in methanol and 180 mL of isopropanol at 80° C. for 1 h. The carboxymethylated fibres were washed with 2 L of deionised water, then a solution of 0.5 mL of acetic acid in 180 mL of deionised water and finally with deionised water. The surface carboxyl groups on the nanocellulose were converted to sodium form by soaking treated fibres in a solution of 8.3 g of sodium bicarbonate in 200 mL of deionised water. Treated samples were finally filtered and washed with deionised water. Dispersions of 5 mg/mL of alkali treated (delignified) and 10 mg/mL bleached fibres after carboxymethyl treatment were homogenised using a laboratory table top GEA homogenizer at 700 bar pressures with two passes. The average NFC diameter of alkali and bleached carboxymethylated samples was 5.6±1.1 nm and 4.2±1 nm, respectively. The introduction of carboxylate ions via this partial carboxymethylation of cellulose fibres resulted in electrostatic repulsion between the nanofibrils and this repulsion makes the nanofibres easier to disperse in elastomer formulations and also limits aggregation of the nanofibres.

Example 8: NFC Obtained After Choline Chloride/Urea Treatment on Sodium Hydroxide Treated (Delignified) Fibres Sodium hydroxide treated (delignified) fibre was added to a solution prepared by heating a choline chloride and urea mixture with a 2:1 molar ratio at 100° C. with the final concentration of 3.7 wt % and stirred for 2 hours at that temperature followed by rinsing with hot water. Dispersions of 0.5 wt % treated fibres in water were then homogenised using a GEA homogenizer at 700 bar pressure for 2 or 4 passes. The average diameter of nanofibers produced from 2 passes of homogenisation was 9±3.2 nm.

Example 9: Bleached CNC

Bleached fibres of nanocellulose were hydrolysed using a 40% (v/v) sulphuric acid solution at 45° C. for 3 hours. To remove excess aqueous acid and the dissolved amorphous segments of the fibres, the digested suspension was centrifuged 4 times at 4750 rpm for 20 minutes, and then dialysed in deionised water until the pH reached 7. The hydrolysed fibre was then re-suspended in deionised water using an ultrasonic probe (Model Q500 Sonicator, from QSonica, Newtown, United States) at 25% amplitude, with a frequency of 20 kHz for 20 minutes with an output energy of 500 W. The obtained nanocrystals had an average diameter of 3.45±0.75 nm and length of 497±106 nm.

Example 10: Positively Charged Bleached NFC Using PDDA

A solution of poly (diallyldimethylammonium chloride) (PDDA) (20 wt %, pH 10) was dropped into a suspension of bleached NFC at the ratio of 1:10 and stirred for 30 min followed by ultasonication for 5 min. In order to remove excess PDDA that was not effectively absorbed on the surface of the NFC, the NFC/PDDA dispersion was centrifuged at a speed of 20,000 rpm followed by rinsing with deionised water. These steps were repeated 3 times. The rinsed NFCs with the positive charge were then redispersed in deionised water using ultrasonication and magnetic stirring.

Some examples for manufacture of nanocomposite elastomer condoms will now be provided.

Example 11: Fabrication of a 0.1 wt % Nanocellulose (Delignified)-Latex Composite Condom Pre-vulcanised natural rubber latex (supplied by Synthomer) was diluted to 45 wt. % solids content by adding to it a dispersion of delignified nanocellulose derived from *Spinifex* grass (nanocellulose described in Example 5) in alkali water (pH 10.5) so that the amount of nanocellulose in the dispersion was 0.1 wt. % of the latex solids content. The latex-nanocellulose dispersion was then stirred using an overhead stirrer at 50 rpm overnight at 25 to 30° C.

Following stirring, a condom-shaped glass former was immersed slowly into the latex-nanocellulose dispersion followed by slow and gradual removal from the latex. The film was dried using hot air and the dipping process was repeated. Following the second dip, the latex-nanocellulose film was dried on the former at 50° C. for 5 minutes in an oven, followed by 125° C. for 5 minutes. The film was then leached in water and final drying at 125° C. was carried out for 25 minutes in an oven. Following drying, the latex-nanocellulose composite condoms containing 0.1 wt. % nanocellulose were removed from the glass formers and their mechanical properties tested. The resultant condoms were parallel-side with smooth texture and 54 mm nominal width. Condom membrane thickness was 45 µm. Air burst pressure was 1.4 kPa with an air burst volume of 38.5 L as tested according to the ISO4074:2002 standard. Tensile testing of the condoms showed stress at break to be 27 MPa and the stress at 500% elongation was 1.9 MPa.

Example 12: Fabrication of a 0.1 wt. % Nanocellulose (Choline Chloride Treated)-Latex Composite Condom Pre-vulcanised natural rubber latex (supplied by Synthomer) was diluted to 45 wt. % solids content by adding to it a dispersion of choline chloride-treated nanocellulose derived from *Spinifex* grass (nanocellulose described in Example 8) in alkali water (pH 10.5) so that the amount of nanocellulose in the dispersion was 0.1 wt. % of the latex solids content. The latex-nanocellulose dispersion was then stirred using an overhead stirrer at 50 rpm overnight at 25 to 30° C.

Following stirring, a condom-shaped glass former was immersed slowly into the latex-nanocellulose dispersion followed by slow and gradual removal from the latex. The film was dried using hot air and the dipping process was repeated. Following the second dip, the latex-nanocellulose film was dried on the former at 50° C. for 5 minutes in an oven, followed by 125° C. for 5 minutes. The film was then leached in water and final drying at 125° C. was carried out for 25 minutes in an oven. Following drying, the latex-nanocellulose composite condoms containing 0.1 wt. % nanocellulose were removed from the glass formers and their mechanical properties tested. The resultant condoms were parallel-side with smooth texture and 54 mm nominal width. Condom membrane thickness was 45 µm. Air burst pressure was 1.3 kPa with an air burst volume of 33 L as tested according to the ISO4074:2002 standard. Tensile testing of the condoms showed stress at break to be 27 MPa and the stress at 500% elongation was 0.7 MPa.

Comparative Example 13

Fabrication of a Nanocellulose-Free (Latex Only) Condom (for Comparison Purposes)

Pre-vulcanised natural rubber latex (supplied by Synthomer) was diluted to 45 wt. % solids content using alkali water (pH 10.5) and stirred using an overhead stirrer at 50 rpm overnight at 25 to 30° C.

Following stirring, a condom-shaped glass former was immersed slowly into the latex dispersion followed by slow and gradual removal from the latex. The film was dried using hot air and the dipping process was repeated. Following the second dip, the latex film was dried on the former at 50° C. for 5 minutes in an oven, followed by 125° C. for 5 minutes. The film was then leached in water and final drying at 125° C. was carried out for 25 minutes in an oven. Following drying, the latex condoms were removed from the glass formers and their mechanical properties tested. The resultant condoms were parallel-side with smooth texture and 54 mm nominal width. Condom membrane thickness was 45 µm. Air burst pressure was 1.1 kPa with an air burst volume of 37.5 L as tested according to the ISO4074:2002 standard.

Example 14: Fabrication of a 0.4 wt. % Nanocellulose (Delignified)-Latex Composite Condom Pre-vulcanised natural rubber latex (supplied by Synthomer) was diluted to 45 wt. % solids content by adding to it a dispersion of delignified nanocellulose derived from *Spinifex* grass (nanocellulose described in Example 5) in alkali water (pH 10.5) so that the amount of nanocellulose in the dispersion was 0.4 wt. % of the latex solids content. The latex-nanocellulose dispersion was then stirred using an overhead stirrer at 50 rpm overnight at 25 to 30° C.

Following stirring, a condom-shaped glass former was immersed slowly into the latex-nanocellulose dispersion followed by slow and gradual removal from the latex. The film was dried using hot air and the dipping process was repeated. Following the second dip, the latex-nanocellulose film was dried on the former at 50° C. for 5 minutes in an oven, followed by 125° C. for 5 minutes. The film was then leached in water and final drying at 125° C. was carried out for 25 minutes in an oven. Following drying, the latex-nanocellulose composite condoms containing 0.1 wt. % nanocellulose were removed from the glass formers and their mechanical properties tested. The resultant condoms were parallel-side with smooth texture and 54 mm nominal width. Condom membrane thickness was 60 μm. Air burst pressure was 1.1 kPa with an air burst volume of 31.5 L as tested according to the ISO4074:2002 standard.

Some examples of thermoplastic polyurethane (TPU)/nanocellulose composite made by solvent casting will now be provided.

Example 15: Preparation of *T. pungens* CNC-Based Nanocomposite

In order to evaluate the property performance of *T. pungens* CNC, a nanocomposite of CNC and an aliphatic TPU (Tecoflex EG-80A with the specific gravity of 1.04 g/cm3 was purchased from Lubrizol (Lubrizol Advanced Materials, Cleveland, Ohio, United States)) was produced. *T. pungens* CNC and TPU were vacuum-dried at 70° C. for 24 hours and TPU polymer was consequently dissolved in dimethylformamide (DMF-EMD chemicals, Saudi Arabia) at room temperature by stirring. A dispersion of freeze-dried CNC in DMF was stirred for 1.5 hours then subjected to ultrasonication at 25% amplitude for 5 minutes, whereby the nanocellulose gel was formed. This procedure was repeated three times until the stable dispersion of CNC in DMF was obtained. Cellulose dispersion was subsequently added to the TPU polymer solution at 1 wt % concentration and mixed overnight at room temperature using a magnetic stirrer. To ensure a high level of mixing prior to casting, the nanocomposite was mixed for a further 5 minutes with an ultrasonic probe at 25% amplitude, followed by stirring for a further 2 hours. Prior to casting, the solution was left to stand, unstirred, for a few minutes in order to degas then casted into a glass mold and oven dried at 60° C. under a nitrogen gas purge for 72 hours. It was important to ensure that the moisture was carefully excluded during casting; otherwise this can result in low-quality cloudy films with inferior mechanical properties. The solvent cast film was then annealed under vacuum at 70° C. for 6 hours to ensure complete removal of any residual solvent. Same procedure was used to cast blank TPU for comparison with the nanocomposite.

Tensile properties of nanocomposite and blank TPU films were measured at room temperature using Instron model 5543 universal testing machine (Instron Pty Ltd., Melbourne, Australia) equipped with a 500 N load cell. Samples were cut into dumbbell shape according to ASTM d-638-M-3 and test was performed with a gauge length of 14 mm and crosshead speed of 50 mm/min. For each sample, five strips were tested. Modulus was determined from the slope of initial low strain meanwhile toughness by integrating the area under the curve.

Figure 3:
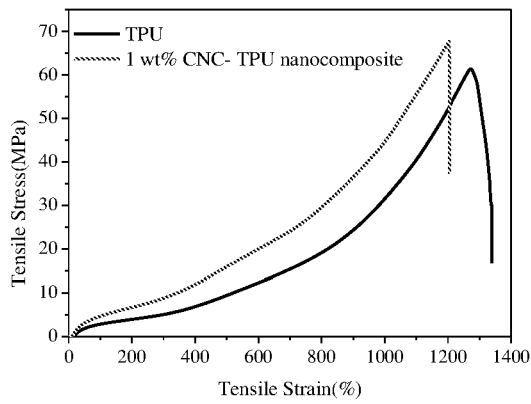
FIG. 3 shows a graph of tensile curves of neat TPU and CNC-TPU nanocomposite material as described in example 15.

A nanocomposite film was prepared from a clear and stable dispersion of strong and high aspect ratio *spinifex* CNC (CNC was obtained from acid hydrolysis using 40% (v/v) acid for 3 hours at 45° C.) in a medium hardness aliphatic thermoplastic polyurethane (TPU) using the solvent casting method. The nanocomposite was then tested under uniaxial extension at room temperature and the results of mechanical properties including ultimate tensile stress, tensile strain at break, Young's modulus and work at fracture (toughness) are presented in FIG. 3 and Table 2, with the neat TPU as a reference. In FIG. 3, the neat TPU is the lower curve and the CNC-containing nanocomposite elastomer is the upper curve. The neat TPU film possessed a typical high elongation at break of about 1268%, a high tensile strength of 61 MPa, and a Young's modulus of 7 MPa. The Young's modulus of this host TPU was increased from 7 MPa to 11.3 MPa by adding 1 wt % CNC due to some stiffening of the elastomer through reinforcement and load transfer by the cellulose crystals network, and the toughness was increased by about 20%. The increases in the modulus and toughness of the composite can be due that the CNC preferentially interacted with the more polar hard segments of the host polyurethane rather than the more hydrophobic soft segments, consequently avoiding the undesired stiffening of the soft microdomains and thereby retaining the large and desirable elongation of polyurethane nanocomposite.

TABLE 2

Mechanical properties of neat TPU and CNC-TPU nanocomposite

| Sample | Young's Modulus (MPa) | Tensile strain (m/m) | Tensile stress (MPa) | Work at fracture (MJ m$^{-3}$) |
|---|---|---|---|---|
| TPU | 7 ± 0.95 | 1256 ± 30 | 59 ± 4.4 | 245 ± 23 |
| TPU, 1 wt% CNC | 11.3 ± 0.3 | 1191 ± 23 | 67 ± 1.5 | 299 ± 19 |

Without wishing to be bound by theory, the present inventors have postulated that the nanocellulose used in the examples given above comprise CNCs and NFCs that have been formed by processing of material derived from arid *Spinifex*. It is possible that these nanocellulose materials have a relatively flexible and amorphous hemicellulose region surrounding the bundle of fibres or individual elementary cellulose nanofibrils and that this hemicellulose region provides an intermediate region between the cellulose fibres and the elastomer which, in turn, allows for flexing between the elastomer and the cellulose fibres. Here, the hemicellulose may be acting as a lubricant between the cellulose fibres and the elastomer molecules, allowing slippage between the two. Thus, although the nanocellulose reinforces the elastomer to result in production of a composite having increased strength, stiffness does not unduly increase. In addition to the high hemicellulose content that may be acting as a lubricant between the cellulose fibres and the elastomer molecules, the hemicellulose which may be present in between elementary cellulose nanofibrils in a nanocellulose fibre may act to render the cellulose fibre itself more flexible. This enhanced flexibility that may be present in nanocellulose with high hemicellulose content makes such nanocellulose materials more suitable than other nanofiller reinforcing agents for use in elastomers where flexibility and elasticity are desired to be retained. The composite material of the present invention may be used in a wide variety of potential uses, including condom manufacture, medical gloves, industrial seals, wear liners in mining applications, tyres, conveyor belts, and balloon manufacture. The material may also be used in other applications. By having increased strength and toughness without unduly increased stiffness, it may be possible to use thinner layers of the composite material to form products such as condoms without weakening the condoms and without increasing the risk of breakage rupture.

The nanocellulose used in the present invention may comprise nanocellulose made in accordance with the methods described in our international patent application number PCT/AU2014/050368, the entire contents of which are incorporated by cross-reference.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. A composite material comprising an elastomer and a nanocellulose material, the nanocellulose material having a hemicellulose content of from 25% to 55% by weight of the nanocellulose material, wherein the nanocellulose material is derived from plants having C4 leaf anatomy, or derived from a drought-tolerant grass species, or derived from an arid grass species.

2. A composite material as claimed in claim 1 wherein the nanocellulose material is derived from plant material and the plant material has a hemicellulose content of from 30 to 55% w/w.

3. A composite material as claimed in claim 1 wherein the nanocellulose material comprises nanocellulose particles or fibres having an aspect ratio of between 250 to 10,000.

4. A composite material as claimed in claim 1 wherein the nanocellulose material is derived from Australian native arid grass known as "*spinifex*" from the genera comprising *Triodia, Monodia*, or from *Digitaria sanguinalis* (L.) Scopoli, *Panicum coloratum* L. var *makarikariense* Goossens, *Brachiaria brizantha* (Hochst. Ex A. Rich) Stapf, *D. violascens* Link, *P. dichotomiflorum* Michaux, *B. decumbens* Stapf, *Echinochloa crus-galli* P. Beauv., *P. miliaceum* L., *B. humidicola* (Rendle) Schweick., *Paspalum distichum* L., *B. mutica* (Forsk.) Stapf, *Setaria glauca* (L.) P. Beauv, *Cynodon dactylon* (L.) Persoon, *Panicum maximum* Jacq., *S. viridis* (L.) P. Beauv, *Eleusine coracana* (L.) Gaertner, *Urochloa texana* (Buckley) Webster, *Sorghum sudanense* Stapf, *E. indica* (L.) Gaertner, *Spodiopogon cotulifer* (Thunb.) Hackel, *Eragrostis cilianensis*(Allioni) Vignolo-Lutati, *Chloris gayana* Kunth, *Eragrostis curvula, Leptochloa dubia, Muhlenbergia wrightii, E. ferruginea* (Thunb.) P. Beauv., *Sporobolus indicus R. Br.* var. *purpureosuffusus* (Ohwi) T. Koyama, *Andropogon gerardii, Leptochloa chinensis* (L.) Nees and *Zoysia tenuifolia* Willd, or from *Anigozanthos, Austrodanthonia, Austrostipa, Baloskion pallens, Baumea juncea, Bolboschoenus, Capillipedium, Carex bichenoviana, Carec gaudichaudiana, Carex appressa, C. tereticaulis, Caustis, Centrolepis, Chloris truncate, Chorizandra, Conostylis, Cymbopogon, Cyperus, Desmocladus flexuosa, Dichanthium sericeum, Dichelachne, Eragrostis, Eurychorda complanata, Evandra aristata, Ficinia nodosa, Gahnia, Gymnoschoenus sphaerocephalus, Hemarthria uncinata, Hypolaena, Imperata cylindrical, Johnsonia, Joycea pallid, Juncus, Kingia australis, Lepidosperma, Lepironia articulate, Leptocarpus, Lomandra, Meeboldina, Mesomelaena, Neurachne alopecuroidea, Notodanthonia, Patersonia, Poa, Spinifex, Themedo triandra, Tremulina tremula, Triglochin, Triodia* and *Zanthorrhoea, Aristida pallens* (Wire grass), *Andropogon gerardii* (Big bluestem), *Bouteloua eriopoda* (Black grama), *Chloris roxburghiana* (Horsetail grass), *Themeda triandra* (Red grass), *Panicum virgatum* (Switch grass), *Pennisetum ciliaris* (Buffel grass), *Schizachyrium scoparium* (Little bluestem), *Sorghatrum nutans* (Indian grass) and *Stipa tenacissima* (Needle grass), wheat straw, or Esparto (provided by *Stipa tenacissima* and *Lygeum spartum*, both Poaceae family), Oyat (which is the French common name for *Ammophila arenaria*, also from the Poaceae family), *Miscanthus* and plants that form tumbleweeds, tumbleweed forming plants from the families Amaranthaceae and Chenopodiaceae), Amaryllidaceae, Apiaceae, Asphodelaceae, Asteraceae, Brassicaceae, Boraginaceae, Caryophyllaceae, Fabaceae, Lamiaceae and Poaceae.

5. A composite material as claimed in claim 4 wherein the nanocellulose material is derived from *T. pungens, T. shinzii, T. basedowii*, or *T. longiceps*.

6. A composite material as claimed in claim 1 wherein the amount of nanocellulose material that is present in the composite material ranges from 0.05% wt to 25% wt (calculated as a weight percentage of the total weight of the nanocellulose material and elastomer components but excluding other chemicals added during compounding.

7. A composite material as claimed in claim 1 wherein the elastomer comprises natural rubber or a polyurethane or polyisoprene (synthetic natural rubber), polybutadiene, polychloroprene, butyl rubber, styrene-butadiene rubber, nitrile rubber, hydrogentated nitrile rubber (HNBR), ethylene propylene rubber, ethylene propylene diene rubber (EPDM), chlorosulphonated polyethylene (CSM), chlorinated polyethylene, polysulphide rubber, ethylene acrylic rubber, fluorocarbon rubber, polytetrafluoroethylene-propylene, epichlorohydrin rubber, polyacrylic rubber, silicone rubber, fluorosilicone rubber, polyphosphazene rubber, polyoctenylene, polypropylene oxide rubber, polynorbornene, polyether block amides, EVA rubber, styrenic block copolymers, SEBS (styrene, ethylene-co-butylene, styrene blocks), SEPS (styrene, ethylene-co-propylene, styrene blocks), SIS (styrene, isoprene, styrene blocks) or segmented elastomers, or copolyester thermoplastic elastomers (TPEs), or any combination of the above elastomers.

8. A composite material as claimed in claim 1 wherein the nanocellulose material comprises nanocellulose particles or fibres having a diameter of up to 20 nm.

9. A composite material as claimed in claim 1 wherein the nanocellulose material comprises nanocellulose particles or fibres comprising primary nanofibrils having a diameter of 3-4 nm.

10. A composite material as claimed in claim 1 wherein the nanocellulose material comprises nanocellulose particles or fibres including essentially no particles or fibres having a diameter of greater than 20 nm.

11. A composite material as claimed in claim 1 wherein the nanocellulose material comprises nanocellulose particles or fibres having a length that falls within the range of from 200 nm up to 10 µm.

12. An article made from the composite material as claimed in claim 1 wherein the article comprises a condom, a pair of gloves, a catheter balloon, a vehicle tire, a component for shoes, a conveyor belt, a wear liner, a component for furniture, a suspension bush, or a blade for windscreen wipers.

13. An article as claimed in claim 12 wherein the article comprises a condom and the elastomer comprises natural rubber latex or polyisoprene and the condom has a tensile strength greater than 31 MPa and a maximum tensile strength of up to 60 Mpa, with a normalised air burst pressure of greater than 0.036 kPa/µm and a maximum normalised air burst pressure of up to 0.007 kPa/µm.

14. A composite material as claimed in claim 1 wherein the nanocellulose material is derived from plant material and the plant material has a hemicellulose content of from 30 to 50% w/w.

15. A composite material as claimed in claim 14 wherein the plant material has a hemicellulose content of from 36 to 48% w/w.

16. A composite material as claimed in claim 14 wherein the plant material has a hemicellulose content of from 40 to 48% w/w.

17. A composite material as claimed in claim 14 wherein the plant material has a hemicellulose content of from 42 to 47% w/w.

18. A composite material as claimed in claim 1 wherein the nanocellulose material comprises nanocellulose particles or fibres having an aspect ratio of between 250 to 5000.

19. A composite material as claimed in claim 1 wherein the nanocellulose material comprises nanocellulose particles or fibres having an aspect ratio of between 250 to 1000.

20. A composite material as claimed in claim 1 wherein the amount of nanocellulose material that is present in the composite material ranges from 0.1% wt to 25% wt (calculated as a weight percentage of the total weight of the nanocellulose material and elastomer components, but excluding other chemicals added during compounding).

21. A composite material as claimed in claim 20 wherein the amount of nanocellulose material that is present in the composite material ranges from 0.2% wt to 20% wt (calculated as a weight percentage of the total weight of the nanocellulose material and elastomer components, but excluding other chemicals added during compounding).

22. A composite material as claimed in claim 20 wherein the amount of nanocellulose material that is present in the composite material ranges from 0.5% wt to 10% wt (calculated as a weight percentage of the total weight of the nanocellulose material and elastomer components, but excluding other chemicals added during compounding).

23. A composite material as claimed in claim 1 wherein the amount of nanocellulose material that is present in the composite material is less than 5% wt (calculated as a weight percentage of the total weight of the nanocellulose material and elastomer components, but excluding other chemicals added during compounding).

24. A composite material as claimed in claim 8 wherein the nanocellulose material comprises nanocellulose particles or fibres having a diameter of up to 15 nm.

25. A composite material as claimed in claim 8 wherein the nanocellulose material comprises nanocellulose particles or fibres having a diameter of up to 10 nm.

26. A composite material as claimed in claim 8 wherein the nanocellulose material comprises nanocellulose particles or fibres having a diameter of up to 5 nm.

27. An article as claimed in claim 13 wherein the condom has a tensile strength greater than 35 MPa and a maximum tensile strength of up to 55 Mpa, with a normalised air burst pressure of greater than 0.040 kPa/µm and a maximum normalised air burst pressure of up to 0.065 kPa/µm.

28. An article as claimed in claim 13 wherein the condom has a tensile strength greater than 40 MPa and a maximum tensile strength of up to 50 MPa, with a normalised air burst pressure of greater than 0.045 kPa/µm and a maximum normalised air burst pressure of up to 0.060 kPa/µm.

29. An article as claimed in claim 13 wherein the condom has a tensile strength greater than 40 MPa and a maximum tensile strength of up to 45 Mpa, with a normalised air burst pressure greater than 0.050 kPa/µm and a maximum normalised air burst pressure up to 0.055 kPa/µm.

* * * * *